United States Patent
Tseng et al.

(10) Patent No.: US 9,388,458 B2
(45) Date of Patent: Jul. 12, 2016

(54) METHODS, SYSTEMS, AND COMPOSITIONS FOR DETECTION OF MICROBIAL DNA BY PCR

(76) Inventors: Ching-Ping Tseng, Tao-Yuan (TW); Shy-Shin Chang, Taipei (TW)

( * ) Notice: Subject to any disclaimer, the term of this patent is extended or adjusted under 35 U.S.C. 154(b) by 580 days.

(21) Appl. No.: 13/475,409

(22) Filed: May 18, 2012

(65) Prior Publication Data

US 2012/0295806 A1 Nov. 22, 2012

Related U.S. Application Data

(60) Provisional application No. 61/487,709, filed on May 19, 2011.

(51) Int. Cl.
*C40B 30/04* (2006.01)
*C12Q 1/68* (2006.01)

(52) U.S. Cl.
CPC .................................. *C12Q 1/6848* (2013.01)

(58) Field of Classification Search
None
See application file for complete search history.

(56) References Cited

U.S. PATENT DOCUMENTS

| 8,828,688 B2 * | 9/2014 | Namsaraev | C12Q 1/6816 435/91.2 |
| 2013/0059761 A1 * | 3/2013 | Jacobson et al. | 506/26 |

OTHER PUBLICATIONS

Harmady et al. (Nature Methods, 2008, 5(3):235-237, Published as manuscript).*

* cited by examiner

*Primary Examiner* — Stephanie K Mummert

(57) ABSTRACT

This invention provides methods, systems, and compositions for detecting low abundance microbial DNA in a sample by PCR. Methods of the present invention are based on a strategy that tags the 5'-end of the target DNA templates with a non-bacterial tagging sequence so as to set the templates apart from the endogenous contaminants present in the PCR reagents. There is also provided fusion probes for tagging the templates and primer sets to amplify the tagged templates. Systems and kits for facilitating and automating methods of the present invention are also provided.

9 Claims, 6 Drawing Sheets

SEQUENCE LISTING

<160> NUMBER OF SEQ ID NOS: 7

<210> SEQ ID NO 1
<211> LENGTH: 53
<212> TYPE: DNA
<213> ORGANISM: Artificial Sequence
<220> FEATURE:
<223> OTHER INFORMATION: fusion probe

<400> SEQUENCE: 1
cagggttttc ccagtcacga cggccgtgtt gaacgtggtc aaatcaaagt tgg    53

<210> SEQ ID NO 2
<211> LENGTH: 21
<212> TYPE: DNA
<213> ORGANISM: Artificial Sequence
<220> FEATURE:
<223> OTHER INFORMATION: Forward primer based on M13 sequence

<400> SEQUENCE: 2
cagggttttc ccagtcacga c    21

<210> SEQ ID NO 3
<211> LENGTH: 25
<212> TYPE: DNA
<213> ORGANISM: Artificial Sequence
<220> FEATURE:
<223> OTHER INFORMATION: Reverse primer based on TstaG765

<400> SEQUENCE: 3
taaccatttc agtaccttct ggtaa    25

<210> SEQ ID NO 4
<211> LENGTH: 30
<212> TYPE: DNA
<213> ORGANISM: Artificial Sequence
<220> FEATURE:
<223> OTHER INFORMATION: Forward primer based on S. aureus fragment

<400> SEQUENCE: 4
aatctttgtc ggtacacgat attcttcacg    30

<210> SEQ ID NO 5
<211> LENGTH: 30
<212> TYPE: DNA
<213> ORGANISM: Artificial Sequence
<220> FEATURE:
<223> OTHER INFORMATION: Reverse primer based on S. aureus fragment

<400> SEQUENCE: 5
cgtaatgaga tttcagtaga taatacaaca    30

<210> SEQ ID NO 6
<211> LENGTH: 53
<212> TYPE: DNA
<213> ORGANISM: Artificial Sequence
<220> FEATURE:
<223> OTHER INFORMATION: Fusion probe based on M13, 16S p201F

<400> SEQUENCE: 6
cagggttttc ccagtcacga cgaggaaggt ggggatgacg tcaaatcatc atg    53

<210> SEQ ID NO 7
<211> LENGTH: 20
<212> TYPE: DNA
<213> ORGANISM: Artificial Sequence

```
<220> FEATURE:
<223> OTHER INFORMATION: Reverse primer based on p1370
<220> FEATURE:
<221> NAME/KEY: misc_feature
<222> LOCATION: (3)..(3)
<223> OTHER INFORMATION: n is deoxyinosine
<220> FEATURE:
<221> NAME/KEY: misc_feature
<222> LOCATION: (8)..(8)
<223> OTHER INFORMATION: n is deoxyinosine

<400> SEQUENCE: 7
agncccgnga acgtattcac                                              20
```

METHODS, SYSTEMS, AND COMPOSITIONS FOR DETECTION OF MICROBIAL DNA BY PCR

CROSS-REFERENCE TO RELATED APPLICATIONS

This application claims the benefit of U.S. Provisional Application 61/487,709 filed on May 19, 2011, the entire content of which is incorporated herein by reference.

SEQUENCE LISTING

This application contains sequence listing.

FIELD OF THE INVENTION

The invention pertains to the field of molecular assays. More particularly, the invention pertains to a PCR-based method for detecting minute amount of microbial DNA and compositions for performing the same.

BACKGROUND OF THE INVENTION

In theory, polymerase chain reaction (PCR) is potentially the most sensitive among all existing methods for rapid detection of microbes in an analyte (e.g. a food sample or a clinical specimen). In cases where detection of a broad range of pathogens is required and some are difficult to culture in vitro or require a long cultivation period, the value of PCR is especially appreciated. For example, by targeting a conserved gene such as the 16S rRNA gene for bacteria or the 18S for eukaryotic pathogens such as fungi, random screening or detection may be achieved using just one PCR reaction. However, in practice, using broad-range PCR to detect minute quantities of microbes is still fraught with many challenges. Some factors that limit the practical application of PCR in microbial detection include the inherent susceptibility of PCR to inhibitors, contamination, and experimental conditions. One of the most difficult and long-standing problems is that of endogenous contamination of PCR reagents.

Reagents for performing PCR, even those available commercially, are obtained from bacterial sources. As such, the reagents, in particular, the Taq DNA polymerases, unavoidably contain some level of DNA contamination from the source bacteria. The contaminating DNA usually include more than one strain or species that cannot be identified as *Thermus aquaticus* or *Escherichia coli*, yet, they bear close homology to the species of *Pseudomonas fluorescens*, *Pseduomonas aeruginosa*, *Alcaligenes faecalis*, or *Azotobacter vinelandii*, all of which are clinically important. As a result, conventional PCR often co-amplifies these contaminants with the target microbial DNA, generating an exceedingly high rate of false positives, thereby, rendering PCR assays so unreliable that they are precluded from clinical applications.

In the past 20 years, numerous attempts have been tried to solve this problem.

Some examples include UV irradiation, restriction endonuclease digestion, ultrafiltration, and pretreatment of reagents with DNase I (ref 20-23). Unfortunately, all previous attempts either failed to completely eliminate false positives due to inherent limitations on reaction conditions or could not achieve the required level of sensitivity due to concomitant inhibition of the PCR reaction. As a result, it is generally believed that broad-range PCR is not clinically relevant, leaving most researchers to pursue multiplex PCR or other non-PCR methods that are expensive, difficult to optimize and cumbersome to perform.

Therefore, there still exists an unmet need to overcome the challenges of utilizing PCR for clinical detection of microbes.

SUMMARY OF THE INVENTION

In view of the above, it is an object of this invention to provide a PCR-based method for detection of microbes in a sample that is sensitive, accurate, inexpensive and easy to perform.

It is also an object of the present invention to provide reagents and diagnostic kits to enable clinical applications of PCR-based molecular diagnostics, particularly in critical care settings.

It is a further object of the present invention to provide a system for performing PCR-based diagnostic assay to detect microbes in clinical specimens and other biological samples.

The above objects of the present invention are satisfied by a novel strategy, herein referred to as PE-PCR, that overcomes the long-standing problem of endogenous contamination in PCR reagents.

Briefly, the PE-PCR strategy recognizes that all previous efforts to solve the endogenous contamination problem had approached the problem heads-on by attempting to remove or destroy the contaminants. For nearly 20 years, such head-on approaches had yielded very little success. In PE-PCR, the inventors dispensed with conventional thinking and devised an indirect approach that ingeniously side-steps the problem of endogenous contamination. Specifically, the PE-PCR strategy uses a DNA fusion probe to add a non-bacterial sequence to the 5'-end of the target templates before any PCR reagent is added to the reaction mix. This way, the target templates are distinguished from the contaminating sequences by their 5'-end non-bacterial sequences. With the aid of a primer complementary to the non-bacterial tagging sequences, the tagged templates can be selectively amplified by standard PCR. Because the non-bacterial fusion primer (a.k.a. fusion probe) will only amplify the 5'-end tagged templates, this renders the bacterial-derived contaminants a non-issue.

Accordingly, a first aspect of the present invention is directed to a method for selectively amplifying one or more target microbial DNA in a sample. Methods in accordance with this aspect of the present invention will make use of one or more DNA fusion probe(s) consisting of a 5'-end portion having a non-bacterial sequence and a 3'-end portion having a sequence complementary to a portion of the target microbial DNA. The methods will generally include the steps of hybridizing the fusion probe(s) to the target microbial DNA in the sample; removing the non-hybridized fusion probe(s) and unbound 3'-end portion of the target microbial DNA; extending the 3'-ends of the fusion probes and the target microbial DNA to form double stranded primer-extended templates; and performing a PCR method to selectively amplify the primer-extended templates with a primer set that includes at least one primer having a non-bacterial sequence complementary to the non-bacterial sequence of the fusion probes.

A second aspect of the present invention is directed to a method for detecting microbial infection in a subject. Methods in accordance with this aspect of the invention will also require a plurality of DNA probes as described above. They will generally include the steps of adding the fusion probes to a sample taken from the subject; hybridizing the fusion probes to microbial DNA in the sample; removing non-hybridized fusion probes and any unbound 3'-end portion of the microbial DNA; extending the 3'-ends of the fusion probes and the microbial DNA to form double stranded primer-extended templates; amplifying the primer-extended templates by performing a PCR method with a primer set that includes at least one forward primer having a non-bacterial sequence complementary to the non-bacterial sequence of the fusion probe; and analyzing the amplified PCR products to determine the presence or absence of a microbe.

A third aspect of the present invention is directed to a fusion probe for generating a primer-extended DNA template from a target microbial DNA in a sample for selective amplification by a PCR method. Fusion probes in accordance with this aspect of the invention generally consist of a 5'-end portion having a non-bacterial sequence and a 3'-end portion having a sequence complementary to a portion of the target microbial sample.

A fourth aspect of the present invention is directed to a kit for generating primer-extended DNA template from a target microbial DNA for selective PCR amplification and detection. Kits in accordance with this aspect of the present invention will generally include a plurality of fusion probes as described above; and a mixture of 3' to 5' exonuclease and Klenow polymerase packaged in an easy to use format.

A fifth aspect of the present invention is directed to a system for detecting a target microbe in a sample. Systems in accordance with this aspect of the invention generally include a sample receiving unit for receiving the sample; a sample processing unit for adding reagents to the sample and maintaining reaction conditions; and a sample analyzing unit for analyzing the processed sample. The sample processing unit is preferably automated and configured to perform the steps of adding a plurality of fusion probes to the sample and maintaining a condition to allow the fusion probes to hybridize with microbial DNA in the sample; adding a degradation/extension reagent to remove non-hybridized fusion probes and unbound 3'-end portion of the hybridized target microbial DNA, and to extend the 3'-ends of the hybridized fusion probes and the target microbial DNA in the 3' to 5' direction so as to generate double stranded primer-extended templates; and adding PCR reagents and maintain reaction conditions to perform amplification of the primer-extended templates; and forwarding the processed sample to the analyzing unit for analysis.

Other aspects and advantages of the invention will be apparent from the following description and the appended claims.

DETAILED DESCRIPTION

Figure 1:
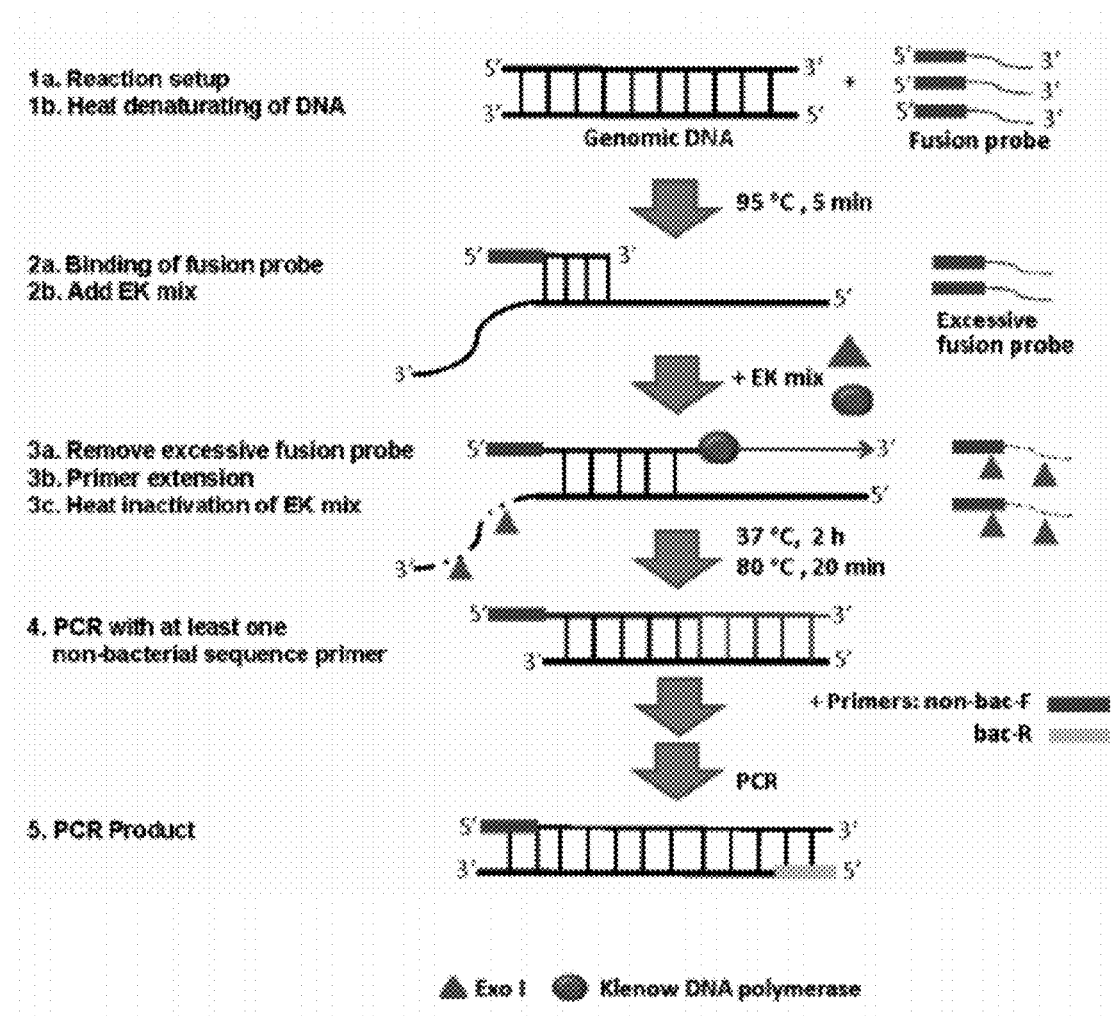
FIG. 1 shows a schematics view of a PE-PCR method in accordance with embodiments of the present invention.

The present invention will now be described in detail by referring to specific embodiments as illustrated in the accompanying figures. Although the present invention will described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims.

DEFINITIONS

Unless otherwise indicated, all terms used herein have the meanings given below, and are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel F M et al. (1993) Current Protocols in Molecular Biology, John Wiley & Sons, New York, N.Y., for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies that might be used in connection with the invention.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescence, paramagnetic particle and the like, which are commercially available from many sources, such as Molecular Probes, Inc., Eugene, Oreg., and Amersham Corp., Arlington Heights, Ill., using techniques that are well known in the art.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

The term "real time PCR" as used herein means that a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is generally based on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehee et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of .sup.32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

General Description of the PE-PCR Strategy

FIG. 1 illustrates schematically how an exemplary PE-PCR experiment works. Starting with step 1a, a sample analyte containing target DNA templates such as the genomic DNA of a microbe is mixed with an excess amount of fusion probes. Each fusion probe consist of a 5'-end portion having a non-bacterial sequence followed by a 3'-end portion having a sequence complementary to a site on the target DNA template.

In step 1b, the sample mixture is heated to denature the DNA templates so that the fusion probes may be hybridized to the target DNA templates (step 2a).

Once the fusion probes are hybridized to their intended targets, a mixture of 3'-end exonuclease and Klenow DNA polymerase (the EK mix) is added to the sample (step 2b). As shown in step 2a, if the hybridization site is not at the very end of the template's 3'-end, a frayed end will form because the non-bacterial portion of the fusion probe will not bond with the template.

In step 3a, the non-bonded portion of the target DNA's 3'-end (the frayed end) along with the unbound excess fusion probes are digested away by the 3'-end exonuclease. After exonuclease digestion, a 5' overhang on the fusion probe strand is created.

In step 3b, the Klenow DNA polymerase will then extend both the fusion probe strand and the template strand in the 5'→3' direction to form blunt ended double strand templates. The strand that extended from the fusion probe will have the non-bacterial tagging sequence located at its 5'-end whereas the strand that extended from the target DNA template will have the non-bacterial tagging sequence located at its 3'-end. This primer extension step can be terminated by heat inactivation of the EK mix.

At this stage, the templates have been tagged with distinguishing sequences and ready to be amplified by PCR. To ensure that only the tagged templates are amplified, the primer set used to run the PCR in step 4 must include at least one forward primer (designated as non-bac-F in FIG. 1) that is complementary to the non-bacterial tagging sequence and a reverse primer (designated as bac-R in FIG. 1) that is complementary to a sequence on the target DNA template downstream of the fusion probe.

The PE-PCR strategy outlined above is simple and can be performed in a single reaction vessel without requiring any other pretreatments of the reagents. It provides a turnkey solution that solves the long-standing problem of endogenous bacterial DNA contamination and is compatible with existing PCR protocols. Based on this strategy, the inventors have devised various methods, systems, compositions, and kits. Those skilled in the art will appreciate that the PE-PCR strategy may be advantageously used in conjunction with any analytical procedures to further quantify or characterize the PCR products. Some exemplary applications of this strategy may include molecular diagnostics of clinical specimens for early detection of bacterial, viral, or fungal infection. Other applications may include forensic applications, bioweapon detection, or archeological sample quantification, but not limited thereto.

Fusion Probes

In general, a fusion probe according to embodiments of the present invention is preferably a forward primer. It will have two components, one encoding a non-bacterial sequence, the other encoding a sequence complementary to a portion of the target DNA. The non-bacterial sequence serves as a tagging sequence to distinguish from endogenous bacterial contaminants in PCR reagents. The complementary sequence serves as a targeting sequence that bonds the fusion probe to the target DNA under hybridization conditions.

Rules for designing an effective fusion probe are generally known in the art. The fusion probe consists of non-bacterial DNA sequence at the 5'-end and the sequences complementary to the microbial target sequence. Due to the possible presence of human genomic DNA during PCR amplification, the 5'-end non-bacterial DNA sequence preferentially does not complementary to the human genomic DNA sequence. Similar strategy applies to the applications related to bacterial DNA detection in the samples from other species. The 3'-end bacterial DNA sequences are complementary to the target gene sequences that universally present in the microbial DNA. The Tm of the 3'-bacteiral sequence is at least 37° C. and at most 95° C. General rule of primer design such as non hairpin sequence is applied for sequence selection.

The tagging sequence may be a sequence derived from a non-bacterial source, or it may be an artificially designed sequence. In some preferred embodiment, the tagging sequence is a viral sequence, preferably one derived from an M13 phage.

The targeting sequence can be a unique sequence that binds the fusion probe to a specific target template or a conversed sequence that binds the fusion probe to a broad-range of microbial DNA. In some exemplary embodiments, the targeting sequence is preferably a conserved sequence from the 16S rRNA gene.

The fusion probes may be manufactured by any methods commonly known in the art, including, but not limited to chemical synthesis.

Detection Methods

Microbial DNA that exist in low abundance in a sample are difficult to detect because the limitations of detection methods and instruments. Using standard PCR to detect low abundance DNA in a sample generally involves selectively amplifying target DNA templates against a sea of noisy background. By replicating the target DNA templates to a large enough quantity, they can then be easily detected. Fusion probes as described above provides a way to effectively distinguish the target DNA from the background noise and undesirable contaminations, thereby, allowing the target DNA to be selectively amplified. Once amplified, a number of analytical tools may then be applied to characterize the amplified nucleic acid products.

Accordingly, methods for detecting microbial infection in a subject in accordance with embodiments of the present invention will generally include the steps of adding the fusion probes to a sample taken from the subject; hybridizing the fusion probes to microbial DNA in the sample; removing non-hybridized fusion probes and any unbound 3'-end portion of the microbial DNA; extending the 3'-ends of the fusion probes and the microbial DNA to form double stranded primer-extended templates; amplifying the primer-extended templates by performing a PCR method with a primer set that includes at least one forward primer having a non-bacterial sequence complementary to the non-bacterial sequence of the fusion probe; and analyzing the amplified PCR products to determine the presence or absence of a microbe.

Preferably, the sample is taken from the subject's bodily flood, such as blood, urine, cerebral spinal fluid, saliva, sputum, or the like. The type of sample taken from the subject is not particularly limited, but will generally correspond to the type of clinical condition the subject is suspected of suffering. For example, in a preferred embodiment, the sample is a blood sample from a subject suspected of suffering from bacteremia. In another preferred embodiment, the sample is a cerebral spinal fluid from a subject suspected of suffering from a bacterial infection that is difficult to culture in vitro (e.g. *Chlamydia pneumoniae*).

Preparation of the sample are typically needed to release the DNA from the microbes. Methods for releasing/extracting microbial DNA are generally known in the art and can be advantageously used to prepare the samples. However, such preparatory steps are not always necessary, depending on the application and specific objectives of the assay.

Hybridization of the fusion probes to the target DNA is generally achieved by heating the sample to above melting temperature ($T_m$) for the target DNA first so that they denature into single stranded DNA and then gradually cool to below Tm to allow binding and annealing to occur. Suitable hybridization conditions are also known in the art and can be routinely determined by those skilled in the art.

Removal of excess fusion probes and 3'-end unbound portion of the target DNA can be achieved by a 3' exonuclease. In a preferred embodiment, the 3' exonuclease is *E. coli* exo I. Other 3' exonuclease may also be suitably used.

Extension of the templates can be achieved by the use of 5' to 3' polymerases. In a preferred embodiment, a 5' to 3' Klenow polymerase is used.

The 3' exonuclease and the 3' to 5' polymerase can be provided in a single mixture (the EK mix) for convenience. Those skilled in the art will appreciate that the optimal ratio of exonuclease and polymerase will depend on the design of the fusion probes as well as the particular exonuclease and polymerase used. Such ratios can be determined by routine optimization experiments and should preferably be done prior to deploying the detection method in clinical settings. To terminate the exonuclease and polymerase activities, a quenching agent can be added or the sample can simply be heated to inactivate the enzymes.

PCR methods are preferably standard PCR using commercially available Taq DNA polymerase and a set of primers that include at least one forward primer having a complementary sequence to the tagging sequence of the fusion probe. Other convention PCR protocols may also be suitably used so long as the protocol is compatible with the primer-extended templates. Methods for performing these conventional PCR are generally known in the art and can be adapted to work with the PE-PCR strategy of the present invention by those skilled in the art. For example, real-time PCR may also be used to simultaneously amplify the primer-extended templates and quantify the abundance of the microbial DNA.

Last but not least, the amplified PCR products can be analyzed by any number of convention analytical methods known in the art to characterize and identify their origin. For example, the melting curve analysis may be applied to the amplified PCR products to generate a melting curve profile. DNA from different microbes will generally have a unique melting curve profile because of their divergent nucleotide content. These melting curve profiles can serve as a sort of "fingerprint" for identifying the origin a sample.

Other analytical methods that can be used include, but not limited to sequencing, microarray assay, mass spectroscopy, melting curve including high-resolution melting analysis, denatured HPLC, capillary electrophoresis, agarose and/or polyacrylamide gel electrophoresis, heteroduplex mobility assay (HMA) and NMR spectroscopy.

Systems and Kits

To perform a PE-PCR method according to the present invention, fusion probes and reagents for removing excess probes as well as extending the hybridized probe/templates are needed in addition to reagents for conventional or real-time PCR. Accordingly, kits of the present invention will include a plurality of pre-made fusion probes and degradation/extension reagents (e.g. EK mix) in a convenient package, such as in a vial or a cartridge, but are not limited thereto. The kit may further include an instruction manual for directing its use or additional reagents for facilitating PCR amplifications.

Figure 6:
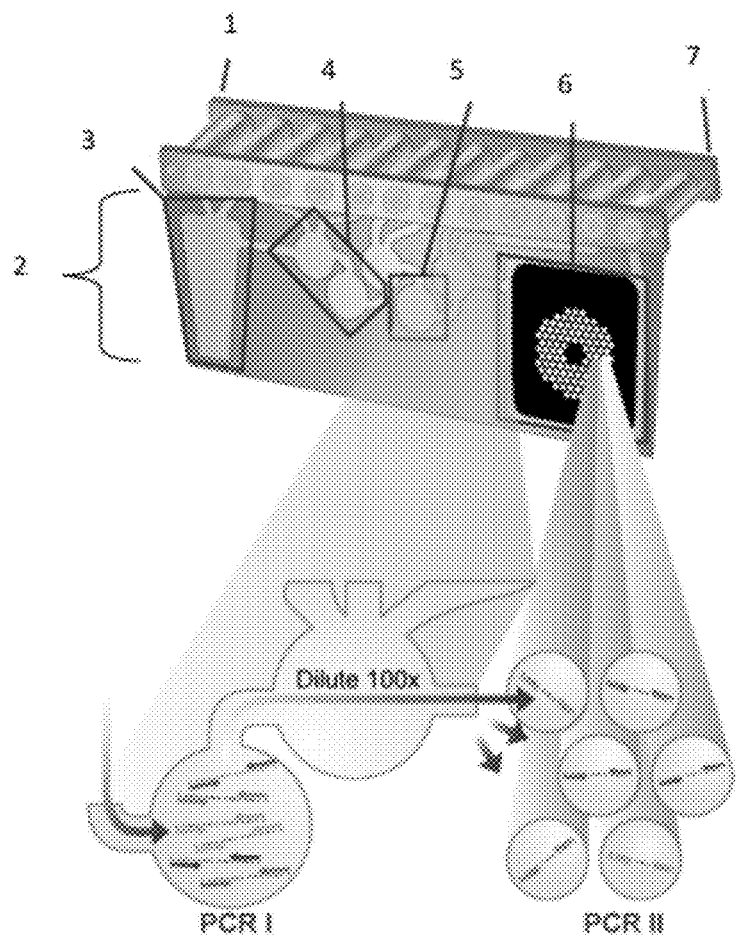
FIG. 6 shows a schematics view of a system in accordance with embodiments of the present invention.

To facilitate high throughput analysis, automated systems may also be constructed to perform detection methods of the present invention. FIG. 6 shows a schematics diagram of an exemplary system of the present invention.

Referring to FIG. 6, a system in accordance with embodiments of the present invention has a sample receiving unit 1 for receiving a sample to be analyzed, a processing unit 2 configured to add various reagents to the sample and maintain appropriate reaction conditions. For example, microbial DNA may be extracted from sample reservoir 3 into reaction chambers 4 and 5 whereto the fusion probes and EK mix may be added so as to form primer-extended templates. The primer-extended templates may then be amplified by PCR in PCR chamber 6. The PCR reaction chamber may then be forwarded to an sample analyzing unit 7.

The processing unit may be configured in a number of different ways. Exemplary means of implementing the processing unit may be a series of microcomputer controlled actuators, or a microfluidic device. The analyzing unit may also be implemented in any number of ways depending on the particular mode of analysis to be applied. For example, it may be a mass spectrometer, a DNA sequencing device, a capillary electrophoretic device, or a melting temperature analysis apparatus. Preferably, systems of the present invention are adapted from existing automated PCR systems such as the BD Max™ system from Becton Dickinson (Franklin Lakes, N.J.).

Non-automated systems may also be assembled using off-shelf components. For example, in an exemplary embodiment, Sample processing may be performed manually or in a separate sample processing/preparation unit. PCR reaction may be performed using a standard thermocycler such as the LightCycler® 480 system by Roche Diagnostics Corporation (Indianapolis, Ind.). Species identification analysis may be performed by high-resolution melting curve analysis using the LightScanner® 32 system (Idaho Technologies, Salt Lake City, Utah).

To further assist the reader in achieving a full and complete appreciation of the present invention, the following illustrative specific examples are provided.

EXAMPLES

Broad-Range Detection of Low Abundance Bacteria by PE-PCR

Several "low-DNA" and HotStart Taq DNA polymerases are available from commercial sources. As a starting point, we first examined 4 commercially available low-DNA or HotStart Taq DNA polymerases to demonstrate that they are not suitable for broad-range amplification of bacterial DNA using the universal primer set p201-p1370.

Figure 2:
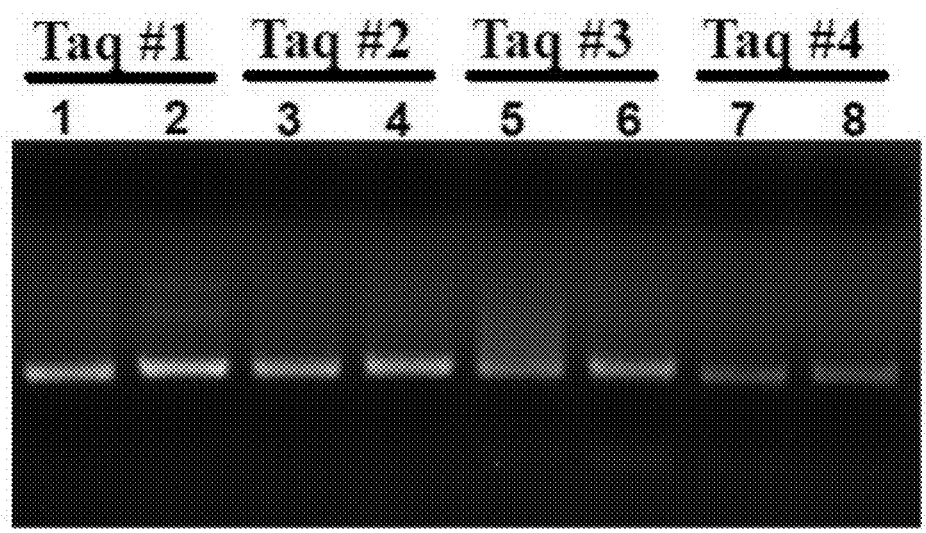
FIG. 2 shows a gel electrophoresis image illustrating that commercially available polymerases are not sufficiently pure for sensitive and specific broad-range amplification of bacterial DNA.

With these polymerases, we performed classical PCR to amplify a sample containing 100 fg of representative *Staphylococcus aureus* bacterial genomic DNA (equivalent to 20 copies of bacterial genome) and a "no template control (NTC)". As shown in FIG. 2, a significant amount of amplified DNA product was found in the NTC reaction, rendering it indistinguishable from the sample reaction. This result confirms that commercially available Taq DNA polymerase and PCR reagents are not sufficiently pure for broad-range bacterial DNA detection in a clinical setting in which detection limits at the fentogram level is usually required.

Figure 3:
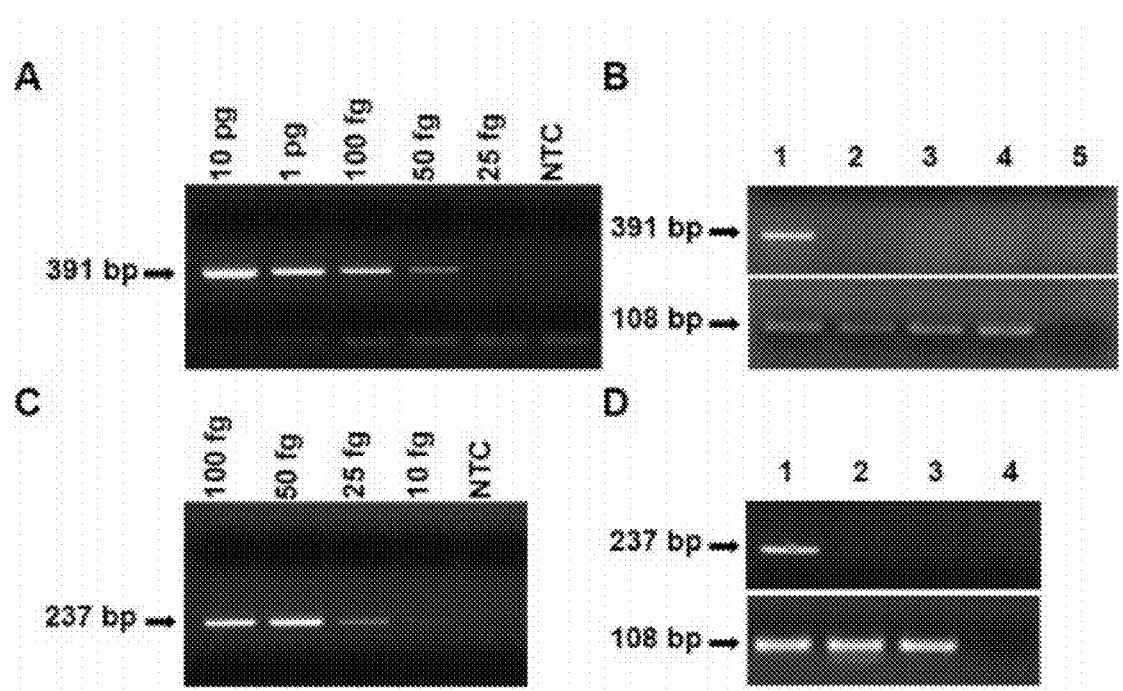
FIG. 3 shows gel electrophoresis images demonstrating that PE-PCR methods in accordance with embodiments of the present invention are capable of specifically amplifying target bacterial DNA without co-amplifying the contaminating bacterial DNA. (A) The indicated amount of S. *aureus* genomic DNA was subjected to PE-PCR using the fusion probe M13-TstaG422 and the primer set M13 and TstaG765. (B) The S. *aureus* genomic DNA (100 fg) was subjected to PE-PCR (upper panel) as described in panel A (lane 1), in the absence of M13 primer (lane 2), and in the artificially contaminating condition by adding 100 fg S. *aureus* genomic DNA into the EK mix (lane 3) or PCR mixtures (lane 4). PE-PCR was also performed in the absence of template DNA (lane 5). The presence of S. *aureus* genomic DNA was confirmed by species-specific PCR that amplified a chromosomal DNA fragment specific for S. *aureus* (lower panel). (C) The indicated amount of S. *aureus* genomic DNA was used as the template for broad-range PE-PCR using the fusion probe M13-16S-p201F and the primer set M13 and p1370. (D) The S. *aureus* genomic DNA (100 fg) was subject to broad-range PE-PCR (upper panel) as described in panel C (lane 1), and in the artificially contaminating condition by adding 100 fg of S. *aureus* genomic DNA into the EK mix (lane 2) or PCR mixtures (lane 3). Broad-range PE-PCR was also performed in the absence of template DNA (lane 4). The presence of S. *aureus* genomic DNA was confirmed by species-specific PCR to amplify a chromosomal DNA fragment of S. *aureus* (lower panel). NTC stands for no template control.

As a proof-of-principle for the PE-PCR strategy, a serially diluted *S. aureus* genomic DNA was subjected to analysis by the strategy. Specifically, the translation elongation factor Tu (Tuf) gene of *S. aureus* was selected as the target for PE-PCR amplification. A fusion probe (M13-TstaG422) was designed with the M13 forward primer sequence at the 5'-end and the Tuf sequences (accession no. AF298796) at the 3'-end (Table 1). After annealing M13-TstaG422 to the template DNA, the EK mix was added into the reaction to degrade the unbound fusion probe and initiate primer extension. The primer extension product was then subjected to PCR amplification using M13 and the downstream primer TstaG765 corresponding to the Tuf genomic sequences. As a result, a 391-bp single PCR product was obtained with 50 fg of bacterial DNA, equivalent to 10 copies of *S. aureus* genome in the sample. In contrast, no PCR product was observed in the NTC control (FIG. 3A). This result indicates that our PE-PCR is accurate and sensitive down to the range of fentograms.

To mimic bacterial DNA contamination of PCR reagent and enzyme, 100 fg of *S. aureus* genomic DNA was spiked into the EK mix and the Taq DNA polymerase-PCR reaction mixture, respectively. Significant amount of PE-PCR product was generated only when template bacterial DNA was present during primer extension (FIG. 3B, lane 1). No PCR product was generated in the NTC reaction (FIG. 3B, lane 5) or when PCR was performed in the absence of M13 primer (FIG. 3B, lane 2). Remarkably, PE-PCR facilitated amplification of template bacterial DNA without co-amplifying the spiking bacterial DNA.

The presence of the spiking DNA in the EK mix or PCR reaction mixture (FIG. 3B, lanes 3 and 4) was verified by *S. aureus* species-specific PCR (FIG. 3B, lower panel). These data indicate no interference from the contaminating bacterial DNA in the PCR reagents and enzymes on specific amplification of the template bacterial DNA and provide a proof-of-principle for our PE-PCR strategy.

To demonstrate the feasibility of PE-PCR in broad-range amplification of bacterial DNA, we designed a universal fusion probe M13-16S-p201F for broad-range PE-PCR of the 16S rRNA gene that is highly conserved among various bacterial species. Serially diluted *S. aureus* genomic DNA was subjected to broad-range PE-PCR using the fusion probe M13-16S-p201F, the M13 forward primer, the p1370 reverse primer (Table 1), and a routinely used HotStart Taq DNA polymerase (Protech) without applying any decontamination pretreatment. A 237-bp single PCR product was obtained and as little as 10 fg of template DNA equivalent to 2 copies of *S. aureus* genomic DNA can be detected by PE-PCR. No PCR product was observed in the NTC reaction (FIG. 3C). Accordingly, the genomic DNAs from a number of clinically important bacterial species have been tested and were shown to be amplifiable by broad-range PE-PCR.

We also mimicked bacterial DNA contamination by spiking 100 fg of *S. aureus* genomic DNA into the EK mix and the Taq DNA polymerase-PCR mixture, respectively. As expected, a positive PE-PCR signal was obtained in the presence of 100 fg template bacterial DNA (FIG. 3D, lane 1), whereas no PCR product was generated in the artificially contaminating condition and NTC reaction (FIG. 3D, lanes 2-4). Again, the presence of the spiking DNA in the reaction mixture was verified by *S. aureus* species-specific PCR (FIG. 3D, lower panel). These data together proves that our PE-PCR strategy enables broad-range detection of bacterial DNA even in the presence of endogenous contamination by the PCR reagents. This is a feat hitherto unattainable.

To explore the detection limit of our strategy, different concentrations of *S. aureus* genomic DNA ranging from 100 fg to 10 fg were subjected to broad-range PE-PCR. The probability of obtaining a positive PCR signal for 100, 50, 25, and 10 fg of template bacterial DNA was 100%, 95%, 65%, and 55%, respectively (n=20). Hence, broad-range PE-PCR is easily performed to specifically amplify template bacterial DNA without compromising detection limit and specificity.

Specific Detection by Coupling PE-PCR with Melting Curve Analysis

Figure 4:
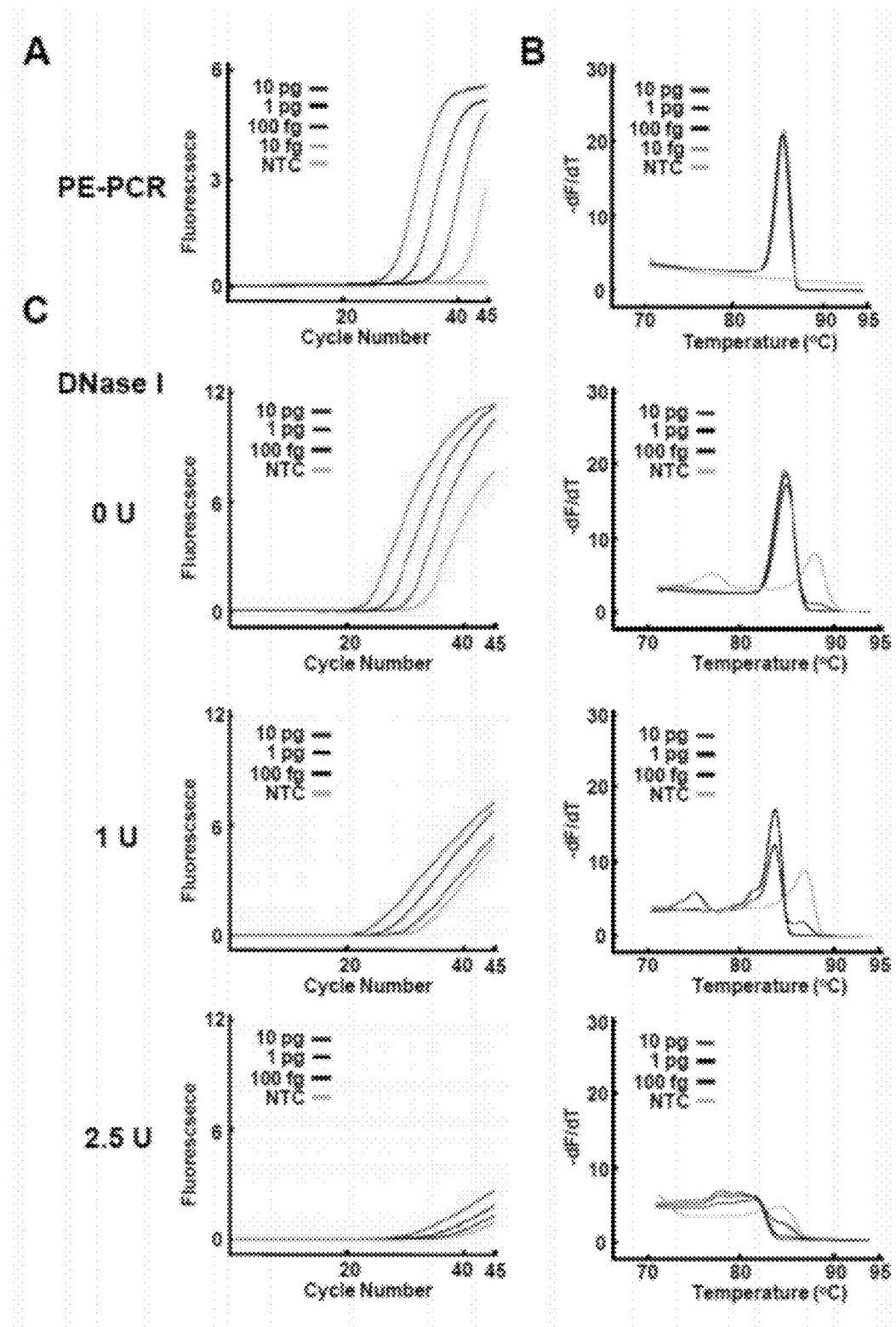
FIG. 4 shows comparison of broad-range real-time PE-PCR and broad-range real-time PCR amplification of template bacterial DNA after pretreatment of PCR reagents with DNase I. (A) The indicated amounts of S. *aureus* genomic DNA were subject to broad-range real-time PE-PCR using the fusion probe M13-16S-p201F and the primer set M13 and p1370 in the presence of LCGreen I plus FIRM dye. (C) Alternatively, the PCR reaction mixtures with or without pretreatment of DNase I (1 U and 2.5 U) were used for real-time PCR to amplify the indicated amounts of S. *aureus* genomic DNA. The PCR products were subject to HRMA using HR-1 instrument. The amplification (all figures on the left column) and derivative plots (all figures on the right column) were shown. NTC stands for no template control.

To further enhance the power of our PE-PCR strategy, we modified the protocol to incorporate real-time PCR and HRMA into the broad-range PE-PCR detection method described above. To demonstrate, a serially diluted *S. aureus* genomic DNA was subjected to broad-range real-time PE-PCR in the presence of HRM dye LCGreen I plus. As revealed by the amplification plots, 10 fg of template DNA resulted in amplicon-specific amplification and no PCR product in the NTC reaction (FIGS. 4A and 4B). The unique nucleotide contents in the PCR amplicon of S. aureus produced a distinctive derivative plot while no melting peak was observed for the NTC reaction. The probability of obtaining a positive PCR signal for 100, 50, 25, and 10 fg of template DNA was 100%, 90%, 50%, and 30%, respectively (n=10).

For comparison, PCR reagents were pretreated with DNase I followed by broad-range PCR amplification of template S. aureus genomic DNA using the primer pair p201 and p1370. As revealed by the amplification and derivative plots (FIG. 4C), the addition of DNase I significantly inhibited PCR amplification. At 1 U of DNase, the endogenous contaminating DNA was not completely eliminated. Increasing the concentration of DNase I to 2.5 U caused further PCR inhibition and hampered the detection limit for broad-range PCR amplification of bacterial DNA.

Figure 5:
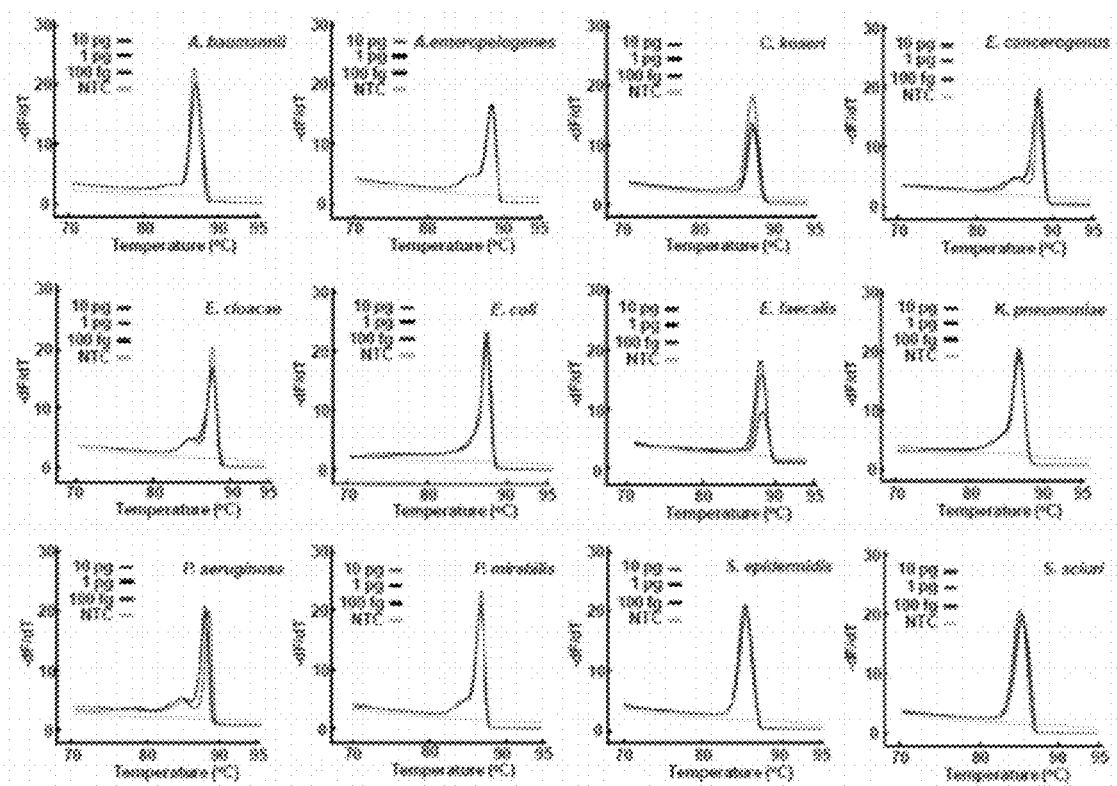
FIG. 5 shows the melting curve plots for broad-range real-time PE-PCR and HRMA for 12 different bacterial species. The indicated amounts of genomic DNA from 12 different bacterial species were subject to broad-range real-time PE-PCR using the fusion probe M13-16S-p201F and the primer set M13 and p1370 in the presence of LCGreen I plus. The PCR product was subject to HRMA using HR-1 instrument and the derivative plots are shown. NTC stands for no template control.

To further validate our strategy, we applied broad-range real-time PE-PCR to analyze additional 12 common bacterial species (Table 2). HRMA of the PCR product using the derivative plots and melting temperature easily distinguished most of the bacterial species (FIG. 5 and Table 2). Using this approach, sequencing of the templates can be largely eliminated to afford more savings and conveniences.

Material and Method

Materials

The exo I and Klenow DNA polymerase were purchased from New England Biolab (Ipswich, Mass.). The LCGreen I plus reagent set and HR-1 instrument were purchased from Idaho Technology (Salt Lake City, Utah). The HotStart Taq DNA polymerase was purchased from Protech (Taipei, Taiwan). The Fast Hot Start Taq DNA polymerase was purchased from KAPA Biosystems (Woburn, Mass.). The "low-DNA" Taq DNA polymerase was purchased from Takara (Shiga, Japan). The ULTRATOOLS Taq DNA polymerase was purchased from Biotools Inc. (Madrid, Spain). The LightCycler capillaries were purchased from Roche Applied Science (Indianapolis, Ind.). The DNase I was purchased from Promega (Madison, Wis.). Bacterial strains were clinical isolates as described previously (ref 11). A complete list of primer and fusion probe sequences is shown in Table 1.

Isolation of Bacterial Genomic DNA

The overnight culture bacterial suspension (4 ml) was centrifuged at 10,000 rpm for 10 min and the pellet was resuspended in 4 ml of solution I buffer (25 mM Tris-HCl, pH 7.5, 50 mM glucose, 10 mM EDTA, and 40 µg/ml lysostaphin). The bacterial suspension was incubated at 37° C. for 2 h and the reaction buffer containing 280 µl of 20% SDS and 40 µl of proteinase K (10 mg/ml) and RNase A (10 mg/ml) was added to the bacterial suspension and incubated at 55° C. overnight. After phenol/chloroform extraction, supernatant was transferred to a clean microcentrifuge tube, and the DNA was precipitated with ethanol. After washing twice with 75% ethanol, DNA pellets were resuspended in water for quantification and the subsequent PCR assays.

PE-PCR

Conventional PE-PCR was performed within one reaction tube. Briefly, the annealing step consisted of a 20 µl annealing mix containing 8 µl of $H_2O$, 5 µl of fusion probe (2 ng/µl), 5 µl of bacterial genomic DNA at the indicated concentration, and 2 µl of 10×PCR buffer. The reaction mixture was heated to 95° C. for 5 min and was kept at 37° C. Then 11 µl of EK mix consisting of 3 µl of $H_2O$, 1 µl of 10×PCR buffer, 5 µl of dNTP (2 mM), 1 µl of Klenow DNA polymerase (5 U/µl), and 1 µl of exo I (20 U/µl) was added to the annealing mix and incubated at 37° C. for 2 h. After heat inactivation at 80° C. for 20 min, the reaction mixture was brought up to 50 µl by adding 14 µl of $H_2O$, 2 µl of 10×PCR buffer, 1 µl of forward primer M13 (5 µM), 1 µl of reverse primer (5 µM), and 1 µl of HotStart Taq DNA polymerase (5 U/µl). The PCR cycling condition was 1 cycle of 95° C. for 10 min, 45 cycles of 95° C. for 15 s, and 60° C. for 1 min. For detection of spiking S. aureus genomic DNA, the M13 and the reverse primer was replaced by the primer set of SA-F and SA-R (Table 1) that specifically amplifies S. aureus genomic DNA fragment (ref 43).

For real-time PE-PCR, the reaction was proportionally scaled down to 8 µl during binding of fusion probe and primer extension. Then the reaction mixture was brought up to 20 µl by adding 1.5 µl of $H_2O$, 2 µl of 10× bovine serum albumin (BSA), 2 µl of 10× LCGreen I plus, 0.8 µl of 10×PCR buffer, 0.4 µl of forward primer M13 (5 µM), 0.4 µl of reverse primer (5 µM), and 0.5 µl of HotStart Taq DNA polymerase (5 U/µl) and was transferred to the capillary tube. Real-time PCR was performed using LightCycler 1.5 instrument and the cycling condition was 1 cycle of 95° C. for 10 min, 45 cycles of 95° C. for 15 s, and 60° C. for 1 min at a transition rate of 20° C./s.

High-Resolution Melting-Curve Acquisition and Analysis

Glass capillaries containing amplification products were transferred to the FIR-1 instrument (Idaho Technology) and the PCR fragments were melted at 64-96° C. at a rate of 0.3° C./s. Melting profiles were assessed with HR-1 software with fluorescence normalization and temperature overlay to superimpose the curves at 0%-20% fluorescence.

Pretreatment of DNase I for Decontamination and Broad-Range PCR Amplification

The PCR reagents containing 2 µl of 10×BSA, 2 µl of dNTP (2 mM), 2 µl of 10× LCGreen I plus, 1 µl of 10×PCR buffer, 0.5 µl of HotStart Taq DNA polymerase (5 U/µl), were incubated with DNase I (1 U or 2.5 U) at 37° C. for 30 min. After heat inactivation of DNase I at 85° C. for 15 min, the reaction mixture was brought up to 20 µl by adding 1 µl of 10×PCR buffer, 2 µl of forward primer p201 (5 µM), 2 µl of reverse primer p1370 (5 µM), and 5 µl of template DNA. The PCR cycling condition was 1 cycle of 95° C. for 10 min, 45 cycles of 95° C. for 15 s, and 60° C. for 1 min at a transition rate of 20° C./s.

Exemplary Diagnostic Kit

In a preferred application, PE-PCR may be used as the basis for a clinical diagnostic assay to test for bacteremia or sepsis. The following table lists reagents that may be included in such a diagnostic kit:

| Reagent | company | Cat. No. | concentration |
|---|---|---|---|
| 10 × BSA | Idaho Technology Inc. | 721007 | 2.5 mg/ml |
| 10 × dNTP | Idaho Technology Inc. | 872306 | 2 mM |
| 10 × PCR buffer | Idaho Technology Inc. | 859506 | 20 mM $MgCl_2$ |
| 10 × LC Green I plus+ | Idaho Technology Inc. | BCHM-ASY-0005 | |
| DNA Polymerase I Lg (Klenow) Fragment | New England Biolab | #M02210 | 5000 U/ml |
| Exonuclease I | New England Biolab | #M0293 | 20000 U/ml |
| 50 mM $MgCl_2$ | invitrogen | 11615-010 | |
| 10 × PCR Rxn Buffer (-$MgCl_2$) | invitrogen | 11615-010 | |
| Hp ™ Hot Start Taq DNA Polymerase | Protech Technology | PT-GL-HTAQ | 5 U/µl |

TABLE 1

The primers and fusion probes sequences.

| Primer/probe type | Primer/probe name | Sequences | Amplicon |
|---|---|---|---|
| *S. aureus* tuf gene (accession number AF298796) | | | |
| Fusion probe | M13-TstaG422 | 5'-CAGGGTTTTCCCAGTCACGAC GGCCGTGTTGAACGTGGTCAAATC AAAGTTGG-3' (SEQ ID No: 1) | 391 bp |
| Forward primer | M13 | 5'-CAGGGTTTTCCCAGTCACGAC-3' (SEQ ID No: 2) | |
| Reverse primer | TstaG765 | 5'-TAACCATTTCAGTACCTTCTGGTAA-3' (SEQ ID No: 3) | |
| *S. aureus*-specific genomic DNA fragment (accession number AF033191) | | | |
| Forward primer | SA-F | 5'-AATCTTTGTCGGTACACGATATT CTTCACG-3' (SEQ ID No: 4) | 108 bp |
| Reverse primer | SA-R | 5'-CGTAATGAGATTTCAGTAGATA ATACAACA-3' (SEQ ID No: 5) | |
| Bacterial 16S rRNA gene | | | |
| Fusion probe | M13-16S-p201F | 5'-CAGGGTTTTCCCAGTCACGAC GAGGAAGGTGGGGATGACGTC AAATCATCATG-3' (SEQ ID No: 6) | 237 bp |
| Forward primer | M13 | 5'-CAGGGTTTTCCCAGTCACGAC-3' (SEQ ID No: 2) | |
| Reverse primer | p1370 | 5'-AGICCCGIGAACGTATTCAC-3' (SEQ ID No: 7) | |
| Forward primer | p201 | 5'-GAGGAAGGIGIGGAIGACGT-3' (SEQ ID No: 8) | |

TABLE 2

High-resolution melting profiles for clinically important bacterial species disclosed by broad-range 16S rRNA PE-PCR.

| Bacterial species (n)[a] | $T_m \pm$ SD (° C.) | GC content (%) | GenBank accession no. |
|---|---|---|---|
| *S. sciuri* (5) | 85.08 ± 0.30 | 48.1 | AB233332 |
| *S. epidermidis* (3) | 85.15 ± 0.31 | 48.1 | L37605 |
| *S. aureus* (5) | 85.25 ± 0.31 | 48.5 | Y15856 |
| *K. pneumoniae* (3) | 86.42 ± 0.27 | 52.3 | AF511429 |
| *P. mirabilis* (3) | 86.64 ± 0.19 | 52.3 | AF008582 |
| *C. koseri* (5) | 86.71 ± 0.21 | 52.7 | EF059880 |
| *A. baumannii* (3) | 87.00 ± 0.11 | 54.9 | AY738399 |
| *E. cloacae* (6) | 87.56 ± 0.21 | 54.0 | DQ089673 |
| *E. coli* (4) | 87.66 ± 0.04 | 54.9 | AF511430 |
| *E. cancerogenus* (4) | 87.71 ± 0.20 | 53.8 | EF011116 |
| *E. faecalis* (6) | 87.84 ± 0.23 | 54.4 | AB292313 |
| *P. aeruginosa* (3) | 87.90 ± 0.21 | 54.8 | Z76672 |
| *A. enteropelogenes* (3) | 88.26 ± 0.04 | 54.8 | EF465529 |

[a] Number of test.

REFERENCES

The following references are each incorporated herein by reference.

1. Rice T W, Bernard G R (2005) Therapeutic intervention and targets for sepsis. Annu Rev Med 56: 225-248.
2. Weile J, Knabbe C (2009) Current applications and future trends of molecular diagnostics in clinical bacteriology. Anal Bioanal Chem 394: 731-742.
3. Klouche M, Schroder U (2008) Rapid methods for diagnosis of bloodstream infections. Clin Chem Lab Med 46: 888-908.
4. Wang Q, Wang S, Beutin L, Cao B, Feng L, et al. (2010) Development of a DNA microarray for detection and serotyping of enterotoxigenic *Escherichia coli*. J Clin Microbiol 48: 2066-2074.
5. Anthony R M, Brown T J, French G L (2000) Rapid diagnosis of bacteremia by universal amplification of 23S ribosomal DNA followed by hybridization to an oligonucleotide array. J Clin Microbiol 38: 781-788.
6. Tissari P, Zumla A, Tarkka E, Mero S, Savolainen L, et al. (2010) Accurate and rapid identification of bacterial species from positive blood cultures with a DNA-based microarray platform: an observational study. Lancet 375: 22430.
7. Tsalik E L, Jones D, Nicholson B, Waring L, Liesenfeld O, et al. (2010) Multiplex PCR to diagnose bloodstream infections in patients admitted from the emergency department with sepsis. J Clin Microbiol 48: 26-33.
8. Tseng C P, Cheng J C, Tseng C C, Wang C, Chen Y L, et al. (2003) Broad-range ribosomal RNA real-time PCR after removal of DNA from reagents: melting profiles for clinically important bacteria. Clin Chem 49: 306-309.
9. Reno W L 3rd, McDaniel D O, Turner W W Jr., Williams M D (2001) Polymerase chain reaction for the detection of bactermia. Am Surg 67: 508-512.
10. Sleigh J, Cursons R, La Pine M (2001) Detection of bacteremia in critically ill patients using 16S rDNA polymerase chain reaction and DNA sequencing. Intensive Care Med 27: 1269-1273.

11. Cheng J C, Huang C L, Lin C C, Chen C C, Chang Y C, et al. (2006) Rapid detection and identification of clinically important bacteria by high-resolution melting analysis after broad-range ribosomal RNA real-time PCR. Clin Chem 52: 1997-2004.
12. Won H, Rothman R, Ramachandran P, Hsieh Y H, Kecojevic A, et al. (2010) Rapid identification of bacterial pathogens in positive blood culture bottles by use of a broad-based PCR assay coupled with high-resolution melt analysis. J Clin Microbiol 48: 3410-3413.
13. Yang S, Ramachandran P, Rothman R, Hsieh Y H, Hardick A, et al. (2009) Rapid identification of biothreat and other clinically relevant bacterial species by use of universal PCR coupled with high-resolution melting analysis. J Clin Microbiol 47: 2252-2255.
14. Corless C E, Guiver M, Borrow R, Edwards-Jones V, Kaczmarski E B, et al. (2000) Contamination and sensitivity issues with a real-time universal 16S rRNA PCR. J Clin Microbiol 38: 1747-1752.
15. Mühl H, Kochem A J, Disqué C, Sakka S G (2010) Activity and DNA contamination of commercial polymerase chain reaction reagents for the universal 16S rDNA real-time polymerase chain reaction detection of bacterial pathogens in blood. Diagn Microbiol Infect Dis 66: 41-49.
16. Bottger E C (1990) Frequent contamination of Taq polymerase with DNA. Clin Chem 36: 1258-1259.
17. Hughes M S, Beck L A, Skuce R A (1994) Identification and elimination of DNA sequences in Taq DNA polymerase. J Clin Microbiol 32: 2007-2008.
18. Maiwald M, Ditton H-J, Sonntag H-G, von Knebel Doeberitz M (1994) Characterization of contaminating DNA in Taq polymerase which occurs during amplification with a primer set for Legionella 5S ribosomal RNA. Mol Cell Probes 8: 11-14.
19. Sontakke S, Cadenas M B, Maggi R G, Diniz P P, Breitschwerdt E B (2009) Use of broad range 16S rDNA PCR in clinical microbiology. J Microbiol Methods 76: 217-225.
20. Ou C Y, Moore J L, Schochetman G (1991) Use of UV irradiation to reduce false positivity in polymerase chain reaction. Biotechniques 10: 442-446.
21. Pandit L, Kumar S, Karunasagar I, Karunasagar I (2005) Diagnosis of partially treated culture-negative bacterial meningitis using 16S rRNA universal primers and restriction endonuclease digestion. J Med Microbiol 54: 539-542.
22. Glushkov S A, Bragin A G, Dymshits G M (2009) Decontamination of polymerase chain reaction reagents using DEAE-cellulose. Anal Biochem 393: 135-137.
23. Silkie S S, Tolcher M P, Nelson K L (2008) Reagent decontamination to eliminate false-positives in *Escherichia coli* qPCR. J Microbiol Methods 72: 275-282.
24. Philipp S, Huemer H P, Irschick E U, Gassner C (2010) Obstacles of multiplex real-time PCR for bacterial 16S rDNA: primer specifity and DNA decontamination of Taq polymerase. Transfus Med Hemother 37: 21-28.
25. Li D, Liu B, Chen M, Guo D, Guo X, et al. (2010) A multiplex PCR method to detect 14 *Escherichia coli* serogroups associated with urinary tract infections. J Microbiol Methods 82: 71-77.
26. Dierkes C, Ehrenstein B, Siebig S, Linde H J, Reischl U, et al. (2009) Clinical impact of a commercially available multiplex PCR system for rapid detection of pathogens in patients with presumed sepsis. BMC Infect Dis 11: 126.
27. Wallet F, Nseir S, Baumann L, Herwegh S, Sendid B, et al. (2010) Preliminary clinical study using a multiplex real-time PCR test for the detection of bacterial and fungal DNA directly in blood. Clin Microbiol Infect 16: 774-779.
28. Lehmann L E, Hunfeld K P, Steinbrucker M, Brade V, Book M, et al. (2010) Improved detection of blood stream pathogens by real-time PCR in severe sepsis. Intensive Care Med 36: 49-56.
29. Steinman C R, Muralidhar B, Nuovo G J, Rumore P M, Yu D, et al. (1997) Domain-directed polymerase chain reaction capable of distinguishing bacterial from host DNA at the single-cell level: characterization of a systematic method to investigate putative bacterial infection in idiopathic disease. Anal Biochem 244: 328-339.
30. McCabe K M, Zhang Y-H, Huang B-L, Eagar E A, McCabe E R B (1999) Bacterial species identification after DNA amplification with a universal primer pair. Mol Gene Metab 66: 205-211.
31. Woo P C, Lau S K, Teng J L, Tse H, Yuen K Y (2008) Then and now: use of 16S rDNA gene sequencing for bacterial identification and discovery of novel bacteria in clinical microbiology laboratories. Clin Microbiol Infect 14: 908-934.
32. Cherkaoui A, Emonet S, Ceroni D, Candolfi B, Hibbs J, et al. (2009) Development and validation of a modified broad-range 16S rDNA PCR for diagnostic purposes in clinical microbiology. J Microbiol Methods 79: 227-231.
33. Champlot S, Berthelot C, Pruvost M, Bennett E A, Grange T, et al. (2010) An efficient multistrategy DNA decontamination procedure of PCR reagents for hypersensitive PCR applications. PLoS One 5: e13042.
34. Spangler R, Goddard N L, Thaler D S (2009) Optimizing Taq polymerase concentration for improved signal-to-noise in the broad range detection of low abundance bacteria. PLoS One 4: e7010.
35. Trevino S, Mahon C R (2000) Bacteremia. In: Mahon C R, Manuselis G, editors. Textbook of diagnostic microbiology. Philadelphia: W.B. Saunders Company. pp. 998-1008.
36. Lin J H, Tseng C P, Chen Y J, Lin C Y, Chang S S, et al. (2008) Rapid differentiation of influenza A virus subtypes and genetic screening for virus variants by high-resolution melting analysis. J Clin Microbiol 46: 1090-1097.
37. Tajiri-Utagawa E, Hara M, Takahashi K, Watanabe M, Wakita T (2009) Development of a rapid high-throughput method for high-resolution melting analysis for routine detection and genotyping of noroviruses. J Clin Microbiol 47: 435-440.
38. Robertson T, Bibby S, O'Rourke D, Belfiore T, Lambie H, et al. (2009) Characterization of Chlamydiaceae species using PCR and high resolution melt curve analysis of the 16S rRNA gene. J Appl Microbiol 107: 2017-2028.
39. Stephens A J, Inman-Bamber J, Giffard P M, Huygens F (2008) High-resolution melting analysis of the spa repeat region of *Staphylococcus aureus*. Clin Chem 54: 432-436.
40. Weinstein M P, Reller L B, Murphy J R, Lichtenstein K A (1983) The clinical significance of positive blood cultures: A comprehensive analysis of 500 episodes of bacteremia and fungemia in adults. I. Laboratory and epidemiologic observations. Rev Infect Dis 5: 35-53.
41. Rello J, Quintana E, Mirelis B, Gurguí M, Net A, et al. (1993) Polymicrobial bacteremia in critically ill patients. Intensive Care Med 9: 22-25.
42. Montgomery J L, Sanford L N, Wittwer C T (2010) High-resolution DNA melting analysis in clinical research and diagnostics. Expert Rev Mol Diag 10: 219-240.
43. Martineau F, Picard F J, Roy P H, Ouellette M, Bergeron M G (1998) Species-specific and ubiquitous-DNA-based assays for rapid identification of *Staphylococcus aureus*. J Clin Microbiol 36: 618-623.

What is claimed is:

1. A method for selectively amplifying one or more target microbial DNA in a sample, comprising:
hybridizing a plurality of fusion probes selected from SEQ ID No.: 1 or SEQ ID No.: 6 to said target microbial DNA, wherein each of said fusion probes consists of a 5'-end portion having a non-bacterial DNA sequence and a 3'-end portion having a sequence complementary to a portion of said target microbial DNA, wherein upon hybridization the 3'-end of the target DNA form a 3'-overhang;
removing non-hybridized fusion probes and the 3'-overhangs of the target microbial DNA;
extending the 3'-ends of the fusion probes and the target microbial DNA to form double stranded primer-extended templates; and
performing a PCR method to selectively amplify the primer-extended templates with a primer set that includes a non-microbial forward primer complementary to the non-bacterial sequence of the fusion probes and a bacterial-reverse primer complementary to a bacterial sequence downstream of the fusion probe.

2. The method of claim 1, wherein the removing step and extending step comprises adding a mixture of exonuclease I and Klenow DNA polymerase.

3. The method of claim 1, wherein said PCR method is selected from standard PCR or real-time PCR.

4. The method of claim 1, wherein said sample is untreated for bacterial DNA contamination.

5. A method for detecting microbial infection in a subject, comprising:
adding a plurality of fusion probes selected from SEQ ID No.: 1 or SEQ ID No.: 6 to a sample of the subject, wherein each of said fusion probes consists a 5'-end portion having a non-bacterial DNA sequence and a 3'-end portion having a sequence complementary to a portion of a target microbial DNA;
hybridizing the fusion probes to microbial DNA in the sample, wherein upon hybridization the microbial DNA form a 3'-overhang;
removing non-hybridized fusion probes and the 3'-overhangs of the microbial DNA;
extending the 3'-ends of the fusion probes and the microbial DNA to form double stranded primer-extended templates;
amplifying the primer-extended templates by performing a PCR method with a primer set that includes at least one forward primer having a non-bacterial sequence complementary to the non-bacterial sequence of the fusion probe and a reverse primer having a sequence complementary to a bacterial sequence downstream of the probe; and
analyzing the amplified PCR products to determine the presence or absence of a microbe.

6. The method of claim 5, wherein said sample is untreated for bacterial DNA contamination.

7. A fusion probe for generating a primer-extended DNA template from a target microbial DNA in a sample for selective amplification by a PCR method, said fusion probe is selected from:
SEQ ID No.:1 or SEQ ID No.:6.

8. A kit for generating primer-extended DNA template from a target microbial DNA for selective PCR amplification and detection, comprising:
a plurality of fusion probes according to claim 7.

9. The kit of claim 8, further comprising a mixture of 3' to 5' exonuclease and Klenow DNA polymerase.

* * * * *